US006312886B1

(12) United States Patent
Lee et al.

(10) Patent No.: US 6,312,886 B1
(45) **Date of Patent: *Nov. 6, 2001**

(54) REACTION VESSELS

(75) Inventors: Martin A. Lee; Hilary Bird, both of Salisbury (GB)

(73) Assignees: The Secretary of State for Defence in Her Brittanic Majesty's Government of the United Kingdom of Great Britain and Northern Ireland; Defence Evaluation & Research Agency, Hamsphire, both of (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/229,748

(22) Filed: Jan. 14, 1999

Related U.S. Application Data

(63) Continuation of application No. PCT/GB97/03187, filed on Nov. 20, 1997.

(30) Foreign Application Priority Data

| | | |
|---|---|---|
| Dec. 6, 1996 | (GB) | 9625442 |
| Jul. 31, 1997 | (GB) | 9716052 |
| Nov. 20, 1997 | (WO) | PCT/GB97/03187 |
| Jan. 16, 1998 | (GB) | 9800810 |

(51) Int. Cl.$^{7}$ .......... C12Q 1/00

(52) U.S. Cl. .......... 435/4; 435/91.2; 435/286.1; 435/283.1; 435/289.1; 435/287.2; 435/288.1; 435/304.1; 422/102; 237/1 R; 237/12; 237/2 A

(58) Field of Search .......... 435/4, 91.2, 283.1, 435/289.1, 286.1, 287.2, 288.1, 304.1; 422/102; 237/1 R, 2 R, 12, 2 A

(56) References Cited

U.S. PATENT DOCUMENTS

| | | | |
|---|---|---|---|
| 4,156,127 | 5/1979 | Sako et al. | 219/301 |
| 4,578,588 | 3/1986 | Galkin . | |
| 4,713,219 | 12/1987 | Gerken et al. . | |
| 4,735,778 | 4/1988 | Maruyama et al. | 422/102 |
| 4,780,246 | 10/1988 | Naarmann | 252/500 |
| 4,878,597 | 11/1989 | Haast . | |

(List continued on next page.)

FOREIGN PATENT DOCUMENTS

| | | |
|---|---|---|
| 2707 641 A1 | 8/1978 | (DE) . |
| 3132926 A1 | 7/1982 | (DE) . |
| 0 124 848 | 11/1984 | (EP) . |
| 0 245 994 | 11/1987 | (EP) . |
| 0 560 721 A2 | 9/1993 | (EP) . |
| 2 210 044 A | 6/1989 | (GB) . |

OTHER PUBLICATIONS

Derwent English abstract for DE 3132926.

*Primary Examiner*—David A. Redding
(74) *Attorney, Agent, or Firm*—Nixon & Vanderhye

(57) ABSTRACT

Apparatus for effecting reactions comprising a plurality of reaction vessels for holding reagents, an electrically conducting polymer which emits heat when an electric current is passed through it, and control device for controlling supply of current to the polymer, the polymer being connectable to an electrical supply via the control device. The control device may be arranged such that different currents and therefore different temperatures can be achieved in each reaction vessel.

Certain novel reaction vessels are described and claimed. The apparatus are reaction vessels may be used in carrying out reactions which require multiple temperature stages such as amplification reactions such as the polymerase chain reaction.

38 Claims, 6 Drawing Sheets

U.S. PATENT DOCUMENTS

| | | | | |
|---|---|---|---|---|
| 5,106,538 | * | 4/1992 | Barma et al. | 252/511 |
| 5,106,540 | | 4/1992 | Barma et al. | 252/511 |
| 5,167,929 | | 12/1992 | Korf et al. . | |
| 5,241,363 | | 8/1993 | Garner | 356/326 |
| 5,485,734 | | 1/1996 | Yang . | |
| 5,498,392 | | 3/1996 | Wilding et al. | 422/68.1 |
| 5,538,848 | | 7/1996 | Livak et al. | 435/5 |
| 5,582,754 | | 12/1996 | Smith et al. | 219/438 |
| 5,601,141 | | 2/1997 | Gordon et al. | 165/263 |
| 5,713,864 | | 2/1998 | Verkaart | 604/113 |
| 5,925,467 | * | 7/1999 | Atrumpler et al. | 428/426 |

* cited by examiner

FIG. 8
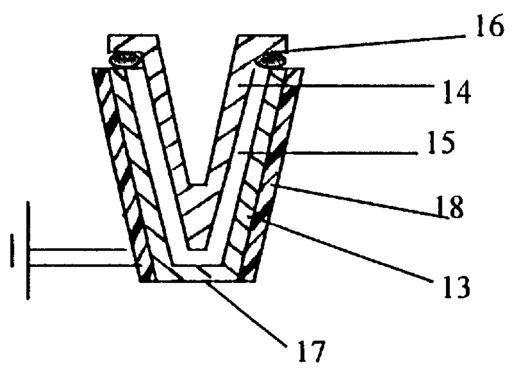
FIG. 9
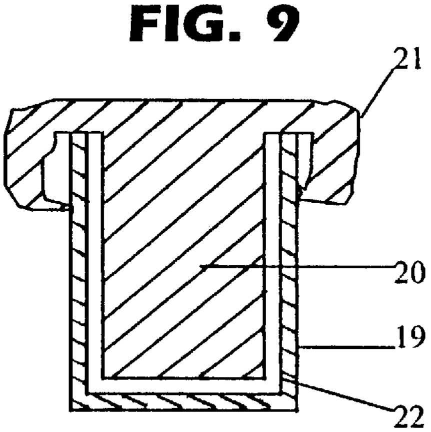
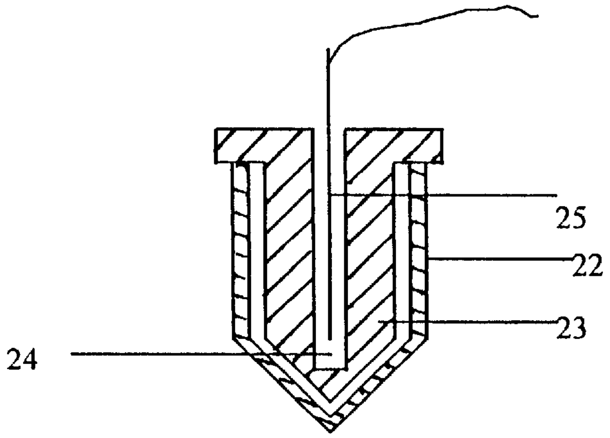
FIG. 10

REACTION VESSELS

This is a continuation in-part of PCT application No. PCT/GB97/03187, filed Nov. 20, 1997.

FIELD OF THE INVENTION

The present invention relates to vessels and apparatus for controlled heating of reagents for example those used in biochemical reactions and to methods for using these.

BACKGROUND OF THE INVENTION

The controlled heating of reaction vessels is often carried out using solid block heaters which are heated and cooled by various methods. Current solid block heaters are heated by electrical elements or thermoelectric devices inter alia. Other reaction vessels may be heated by halogen bulb/turbulent air arrangements. The vessels may be cooled by thermoelectric devices, compressor refrigerator technologies, forced air or cooling fluids. The reaction vessels fit into the block heater with a variety of levels of snugness. Thus, the thermal contact between the block heater and the reaction vessel varies from one design of heater to another. In reactions requiring multiple temperature stages, the temperature of the block heater can be adjusted using a programmable controller for example to allow thermal cycling to be carried out using the heaters.

This type of heater arrangement is particularly useful for reactions requiring thermal cycling, such as DNA amplification methods like the Polymerase Chain Reaction (PCR). PCR is a procedure for generating large quantities of a particular DNA sequence and is based upon DNA's characteristics of base pairing and precise copying of complementary DNA strands. Typical PCR involves a cycling process of three basic steps.

Denaturation: A mixture containing the PCR reagents (including the DNA to be copied, the individual nucleotide bases (A,T,G,C), suitable primers and polymerase enzyme) are heated to a predetermined temperature to separate the two strands of the target DNA.

Annealing: The mixture is then cooled to another predetermined temperature and the primers locate their complementary sequences on the DNA strands and bind to them.

Extension: The mixture is heated again to a further predetermined temperature. The polymerase enzyme (acting as a catalyst) joins the individual nucleotide bases to the end of the primer to form a new strand of DNA which is complementary to the sequence of the target DNA, the two strands being bound together.

A disadvantage of the known block heaters arises from the lag time required to allow the heating block to heat and cool to the temperatures required by the reaction. Thus, the time to complete each reaction cycle is partially determined by the thermal dynamics of the heater in addition to the rate of the reaction. For reactions involving numerous cycles and multiple temperature stages, this lag time significantly affects the time taken to complete the reaction. Thermal cyclers based on such block heaters typically take around 2 hours to complete 30 reaction cycles.

For many applications of the PCR technique it is desirable to complete the sequence of cycles in the minimum possible time. In particular for example where respiratory air or fluids or foods for human and animal stock consumption are suspected of contamination rapid diagnostic methods may save considerable money if not health, even lives.

An alternative thermal cycler contains a number of capillary reaction tubes which are suspended in air. The heating and cooling of the reaction tubes is effected using a halogen lamp and turbulent air from a fan. The thermal dynamics of this system represent a considerable improvement over the traditional block heater design because heated and cooled air is passed across the reaction tubes and the required temperatures are achieved quite rapidly, the fan providing a homogeneous thermal environment and forced cooling. Using this apparatus 30 reaction cycles can be completed in about 15 minutes.

A disadvantage of this thermal cycler is that air cooling and heating are not readily suitable in apparatus which is required to provide different thermal cycling conditions to multiple reactions at the same time, and is certainly not mobile or portable.

SUMMARY OF THE INVENTION

The applicants have developed an efficient system for rapid heating and cooling of reactants which is particularly useful in thermal cycling reactions.

The present invention relates to a reaction vessel comprising an electrically conducting polymer which emits heat when an electric current is passed through it.

Thus in a first aspect, there is provided apparatus for effecting reactions, said apparatus comprising a plurality of reaction vessels for holding reagents, an electrically conducting polymer which emits heat when an electric current is passed through it, and control means for controlling supply of current to the polymer, the polymer being connectable to an electrical supply via the control means.

Further aspects of the invention include specific reaction vessels used in the apparatus as detailed hereinafter as well as methods for carrying out chemical or biochemical reactions.

Electrically conducting polymers are known in the art and may be obtained from Caliente Systems Inc. of Newark, U.S.A. Other examples of such polymers are disclosed for instance in U.S. Pat. Nos. 5,106,540 and 5,106,538. Suitable conducting polymers can provide temperatures up to 300° C. and so are well able to be used in PCR processes where the typical range of temperatures is between 30° and 100° C.

An advantage of the invention over a conventional block heater is derived from the fact that polymers which conduct electricity are able to heat rapidly. The heating rate depends upon the precise nature of the polymer, the dimensions of polymer used and the amount of current applied. Preferably the polymer has a high resistivity for example in excess of 1000 ohm.cm. The temperature of the polymer can be readily controlled by controlling the amount of electric current passing through the polymer, allowing it to be held at a desired temperature for the desired amount of time. Furthermore, the rate of transition between temperatures can be readily controlled after calibration, by delivering an appropriate electrical current, for example under the control of a computer programme.

Furthermore as compared to a block heater, rapid cooling can also be assured because of the low thermal mass of the polymer. If desired however, the reaction vessel may be subjected to artificial cooling to further increase the speed of cooling. Suitable cooling methods include forced air cooling, for example by use of fans, immersion in ice or water baths etc.

In addition, the use of polymer as the heating element in a reaction vessel will generally allow the apparatus to take a more compact form than existing block heaters, which is useful when carrying out chemical reactions in field conditions such as in the open air, on a river, on a factory floor or even in a small shop.

Each reaction vessel may take the form of a reagent container such as a glass, plastics or silicon container, with electrically conducting polymer arranged in close proximity to the container. In one embodiment of the vessel, the polymer is provided as a sheath which fits around the reaction vessel, in thermal contact with the vessel. The sheath can either be provided as a shaped cover which is designed to fit snugly around a reaction vessel or it can be provided as a strip of film which can be wrapped around the reaction vessel and secured.

The polymer sheath arrangement means that close thermal contact is achievable between the sheath and the reaction vessel. This ensures that the vessel quickly reaches the desired temperature without the usual lag time arising from the insulating effect of the air layer between the reaction vessel and the heater. Furthermore, a polymer sheath can be used to adapt apparatus using pre-existing reaction vessels. In particular, a strip of flexible polymer film can be wrapped around a reaction vessel of various different sizes and shapes.

Where a sheath is employed it may be advantageous for it to be perforated or in some way reticulated. This may increase the flexibility of the polymer and can permit even readier access by a cooling medium if the polymer is not itself used to effect the cooling.

Alternatively the polymer maybe provided as an integral part of the reaction vessel. The reaction vessel may be made from the polymer by extrusion, injection moulding or similar techniques. Alternatively, the reaction vessel may be manufactured using a composite construction in which a layer of the conducting polymer is interposed between layers of the material from which the vessel is made or in which the internal or external surfaces of the reaction vessel is coated with the polymer, or again in which the vessel is basically made of the polymer coated with a thin laminate of a PCR compatible material. Such vessels may be produced using lamination and/or deposition such as chemical or electrochemical deposition techniques as is conventional in the art.

Vessels which comprise the polymer as an integral part may provide particularly compact structures.

If several reaction vessels are required for a particular reaction, any electrical connection points can be positioned so that a single supply can be connected to all the reaction vessels or tubes. The reaction vessels may be provided in an array.

Alternatively, each of or each group of reaction vessels may have its own heating profile set by adjusting the applied current to that vessel or group of vessels. This provides a further and particularly important advantage of reaction vessels with polymer in accordance with the invention over solid block heaters or turbulent air heaters, in that individual vessels can be controlled independently of one another with their own thermal profile. It means that a relatively small apparatus can be employed to carry out a plurality of PCR assays at the same time notwithstanding that each assay requires a different thermal profile i.e. a varying operating temperature and/or dwell times in each stage of a cycle. For example, PCR tests for detecting a fair plurality of organisms in a sample can be carried out simultaneously, notwithstanding that the nucleotide sequence which is characteristic of each organism is amplified at different PCR operating temperatures.

The polymer may suitably be provided in the form of a sheet material or film, for example of from 0.01 mm to 10 mm, such as from 1 to 10 mm, and preferably 0.1 to 0.3 mm thick. By using thin films, the volume of polymer required to cover a particular reaction vessel or surface is minimised. This reduces the time taken for the polymer to heat to the required temperature as the heat produced by passing the current through the polymer does not have to be distributed throughout a large volume of polymer material.

In use, the polymer component of the reaction vessel is arranged such that an electric current can be generated within the polymer. This can either be achieved by providing the polymer with connection points for connection to an electrical supply or by inducing an electric current within the polymer, for example by exposing the polymer to suitable electrical or magnetic fields.

The close thermal contact between the polymer and the reagents or reagent container which may be established in the reaction vessels of the invention reduces or eliminates the insulating effect of the air layer between the heating element and the reaction vessel.

The vessel may comprise a flat support plate such as a two-dimensional array in particular a chip such as a silicon wafer chip; or a slide, in particular a microscope slide, on which reagents may be supported. The plate may be made from the polymer or the polymer may be provided as an integral part of the plate, either as a coating on one side of the plate or as a polymer layer within a composite construction as previously described. Where appropriate, and particularly when the plate is a chip, the polymer may be deposited and/or etched in the preferred format on the chip using for example printed circuit board (PCB) technology.

Where the reaction vessel comprises a slide or chip, the apparatus may comprise the slide or chip, an electrical supply, means for connecting the electrical supply to the slide or chip or for inducing an electrical current in the polymer and a means for controlling the current passing through the polymer layer in the slide or chip.

Vessels of this type may be particularly useful for carrying out in-situ PCR for example on tissue samples.

These vessels are novel. Thus in a further aspect the invention provided a reaction vessel comprising a slide or a chip and an electrically conducting polymer which emits heat when an electric current is passed through it, said polymer being arranged to heat reactants on said slide or chip.

Other suitable reaction vessels are tubes and cuvettes, which are known in the art.

In a preferred embodiment of the invention, the vessel comprises a capillary tube. The heat transfer from a capillary tube to reagents contained within it is more rapid than that achieved using conventional reagent vessels as the surface area to volume ratio of the reagents in the capillary tube is larger than in a conventional reagent vessel. Furthermore, the volume of samples used in these reactions is frequently very small, of the order of microliters or less and small volume vessels are thus essential.

Also, the invention provides apparatus for carrying out reaction at controlled temperatures, which apparatus comprises a reaction vessel comprising a slide or chip and a means for controlling the supply of electric current to the electricity conducting polymer so as to control the temperature thereof.

Capillary tube reaction vessels are usually filled by allowing the sample to be drawn into the tube under capillary action. The ends of the tube are then sealed. In the case of a glass tube, which is the usual form, sealing is typically effected thermally.

This thermal sealing method has a major disadvantage in being liable to degrade the sample. Also however, a glass tube of what might well be less than 2 mm outside diameter and about 4 cm length, is very fragile. There are capillary reaction vessels which have one end presealed. These may be filled by employing centrifuge or vacuum techniques. These are however time consuming and besides entail a risk of retained air and contamination from air.

It is not uncommon for a newly opened box to contain four or five broken tubes in a bank of 96 such vessels, which is one popular quantity for use in biochemical thermocycling apparatus. Further breakages are very likely to occur during filling and mounting and even in use, not least because heating and cooling is typically effected using turbulent hot and cold air.

There exist also reaction vessels formed from plastics material and vessels which are not capillary in form. Such vessels typically have a maximum internal diameter of 5 to 10 mm and are conical or paraboloid tapering down to the base. These are relatively easily filled and are provided with caps which seal thereto. They are relatively unbreakable but have the disadvantage that the required temperatures may not be accurately attained or consistently attained throughout the sample or with each cycle. Because of the low surface area to volume ratio, heat transfer is poor in conventional tubes.

Reaction vessels in which a cap for a reaction vessel projects into the vessel in order to reduce the volume thereof are described for example in EP-A-245994 and U.S. Pat. No. 4,578,588.

In a particularly preferred embodiment, the reaction vessel used in the present invention comprises a container, a cap member, and an electrically conducting polymer which is arranged so as to heat reagents in the reaction vessel when current is supplied to said polymer, the cap member being formed so as to project into the container to reduce the capacity thereof and to create a space therebetween of substantially consistent proportions.

Thus in a further aspect the invention provides a reaction vessel comprising a container, a cap member, and an electrically conducting polymer which is arranged so as to heat reagents in the reaction vessel when current is supplied to said polymer, the cap member being formed so as to project into the container to reduce the capacity thereof and to create a space therebetween of substantially consistent proportions.

In this way, the insertion of the cap member into the vicinity of the sample results in an increase in the surface area to volume ratio of the sample, so that the required temperature can be consistently and rapidly attained throughout the reagent mass. In addition the reaction vessel which is easy to fill.

The expression "substantially consistent proportions" used herein means that the space, which will form the reagent volume is of substantially similar cross section throughout. This means that externally applied factors such as heating or cooling means, will be effective throughout the entire volume of the reagent in a substantially consistent manner.

As before, the reaction vessel of this embodiment may take the form of a reagent container such as a glass or plastics container, with electrically conducting polymer arranged in close proximity to the container. In one embodiment of the vessel, the polymer is provided as a sheath which fits around the reaction vessel, in thermal contact with the vessel. The sheath can either be provided as a shaped cover which is designed to fit snugly around a reaction vessel or it can be provided as a strip of film which can be wrapped around the reaction vessel and secured.

In a preferred arrangement, the polymer is provided as an integral part of the reaction vessel, and in this case, it may either be as part of the container or the cap member. The container and/or cap member may be made from the polymer by extrusion, injection moulding or similar techniques. Alternatively, the container or cap member may be manufactured using a composite construction in which a layer of the conducting polymer is interposed between layers of the material, such as plastics or glass, from which the container or cap member is made. In a further alternative, the internal or external surfaces of the container and/or cap member are coated with the polymer. Alternatively, the container or cap member is basically made of the polymer coated with a thin laminate of a PCR compatible material. Such vessels may be produced using lamination and/or deposition such as chemical or electrochemical deposition techniques as is conventional in the art.

Reaction vessels and apparatus of the invention can be used in a variety of situations where chemical or biochemical reactions are required to be carried out. Thus the invention further provides a method of carrying out a reaction such as a chemical or biochemical reaction which method comprises heating reagents in apparatus or in a reaction vessel as described above.

In particular the invention provides a method of carrying out a chemical or biochemical reaction which requires multiple temperature stages; said method comprising placing reagents required for said reaction in a reaction vessel which comprises an electrically conducting polymer which emits heat when an electric current is passed through it, supplying current to said polymer so as to heat reagents to a first desired temperature; and thereafter adjusting the current so as to produce the subsequent temperatures stages required for the reaction.

As well as amplification reactions such as PCR reactions already mentioned above, the vessels and apparatus of the invention can be used for the purposes of nucleic acid sequencing and in enzyme kinetic studies wherein are studied the activity of enzymes at various temperatures, likewise other reactions, especially those involving enzymic activity, where precise temperatures need to be maintained. The reaction vessels of the invention allow precise temperatures to be reached and maintained for suitable time periods, and then changed rapidly as desired, even in mobile or portable apparatus in accordance with some embodiments of the invention.

For PCR reactions, the temperature conditions required to achieve denaturation, annealing and extension respectively and the time required to effect these stages will vary depending upon various factors as is understood in the art. Examples of such factors include the nature and length of the nucleotide being amplified, the nature of the primers used and the enzymes employed. The optimum conditions may be determined in each case by the person skilled in the art. Typical denaturation temperatures are of the order of 95° C., typical annealing temperatures are of the order of 55° C. and extension temperatures of 72° C. are generally of the correct order. When utilising the reaction vessels and apparatus of the invention, these temperatures can rapidly be attained and the rate of transition between temperatures readily controlled.

Generic DNA intercalating dyes and strand specific gene probe assays, e.g. Taqman® assays as described in U.S. Pat. No. 5,538,848 and Total Internal Reflection Fluorescence (TIRF) assays such as those described in WO93/06241 can of course be employed with many embodiments of the invention. In such assays, a signal from the sample such as a fluorescent signal or an evanescent signal is detected using a fluorescence monitoring device. When this type of process is undertaken, the fluorescence monitoring device must be arranged such that it is able to detect signal emanating from the sample. In some instances, it may be helpful if at least a part of the vessel, for example an end where the vessel is a tube of the invention may be optically clear so that measurements can be made through it. Alternatively the vessel can be provided with means of conveying a signal from the sample to the monitoring device, for example, an optic fibre or an evanescent wave guide.

The fluorescence monitoring device may be set to read a fluorescent signal at one or more wavelengths depending upon the nature of the signally system being used.

DETAILED DESCRIPTION OF THE INVENTION

Embodiments of the present invention will now be described, by way of example, with reference to the accompanying drawings, wherein FIG. 1 Shows a reaction vessel heater comprising a sheath of electrically conducting polymer arranged to fit around a reaction tube;

Figure 7:
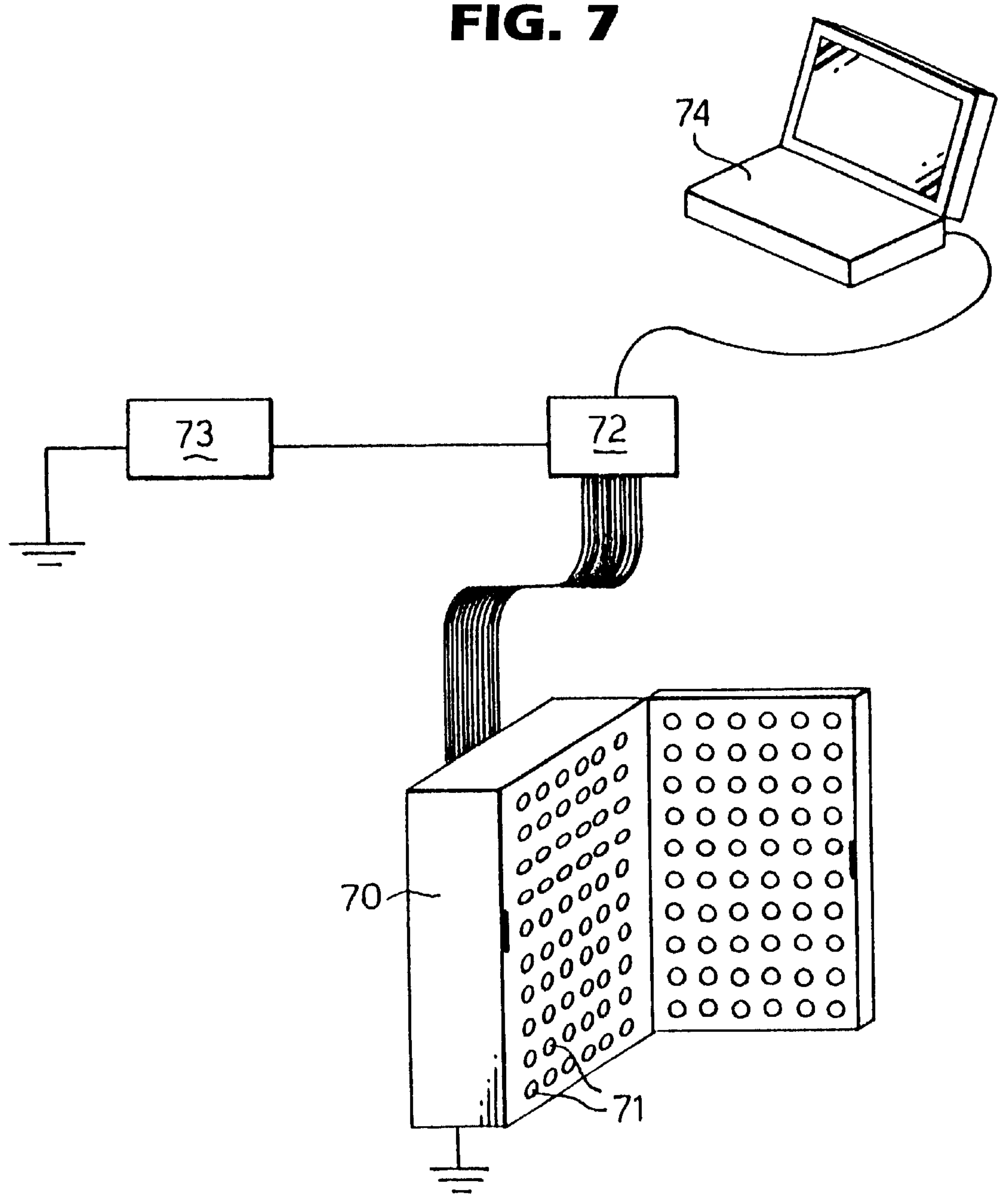
FIG. 7 is a schematic diagram of a portable PCR multidetector.
Figure 7A:
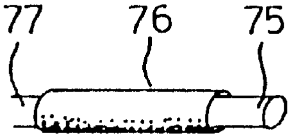
Figure 11:
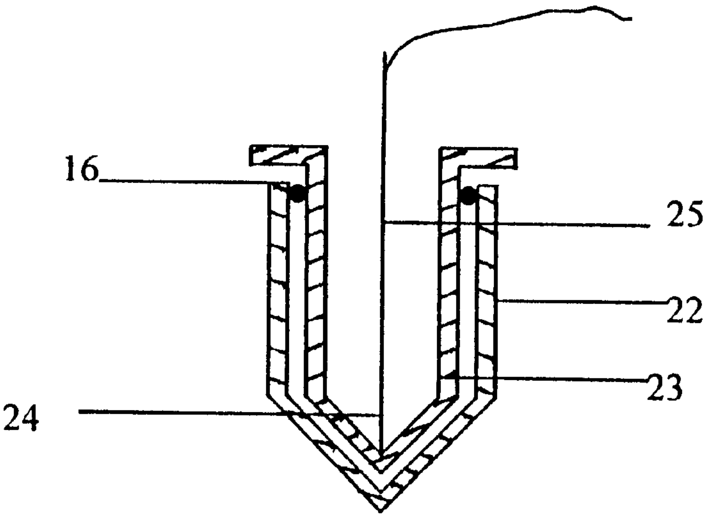
Figure 12:
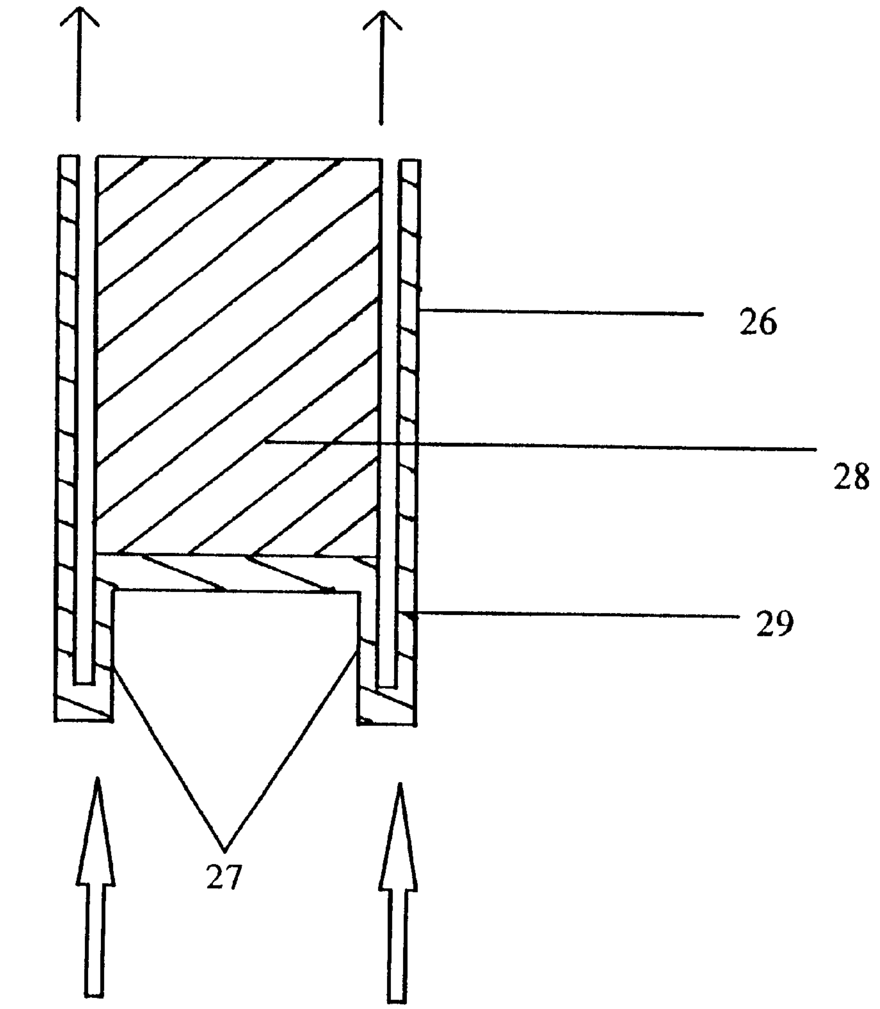

FIG. 7*a* is a diagram of a detector element for use in the apparatus of FIG. 7;

FIG. 8 shows a section through a first embodiment of a reaction vessel of the invention;

FIG. 9 shows a section through a different embodiment of a reaction vessel of the invention;

FIG. 10 shows a section through yet a further embodiment of a reaction vessel of the invention;

FIG. 11 shows a section through a modified embodiment of the reaction vessel of FIG. 10; and FIG. 12 shows a section through an embodiment of a reaction vessel of the invention which allows reaction monitoring to be effected readily.

Figure 1:
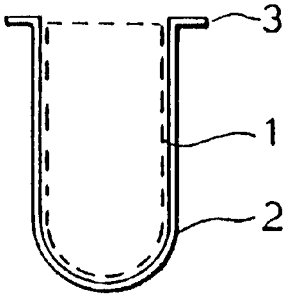

Referring to FIG. 1, a sheath of electrically conducting polymer 2 is provided with electrical connection points 3 for connection to an electrical supply. The size and shape of the sheath 2 is determined by the dimensions and shape of a reaction vessel 1 around which the sheath fits.

In use, the sheath 2 is placed around and in close thermal contact with the reaction vessel 1. The connection points 3 are then connected to an electrical supply (not shown) and current is passed through the polymer sheath 2, thereby heating it and any reagents inside the reaction vessel 1.

Figure 2:
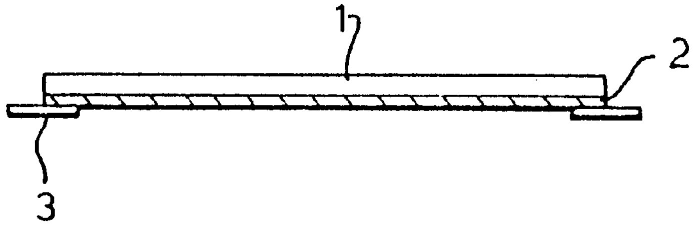
FIG. 2 Shows a reaction slide having an electrically conducting polymer coating over one of its surfaces.

Referring to FIG. 2, a slide 1 is coated on one side with electrically conducting polymer 2. Electrical connection points 3 are provided at either end of the slide 1, in electrical connection with the polymer layer 2.

Figure 3:
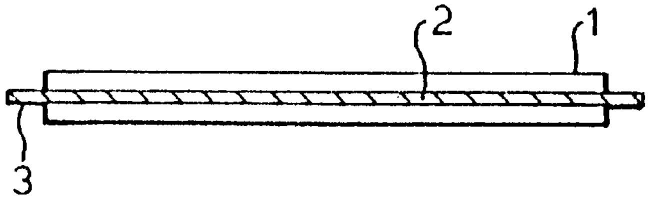
FIG. 3 Shows a reaction slide having a layer of electrically conducting polymer within a composite construction.

In FIG. 3, the vessel comprises a slide 1 having a composite construction such that a layer of electrically conducting polymer 2 is interposed between layers of the usual material used to produce such slides such as glass. Electrical connection points 3 are provided at either and of the slide 1, in electrical connection with the polymer layer 2.

In use, an electrical supply (not shown) is connected to the electrical connection points 3 on the slide shown in FIGS. 2 and 3 and current is passed through the polymer layer 2, thereby heating the slide 1 and any reagents placed on the slide 1.

Figure 4:
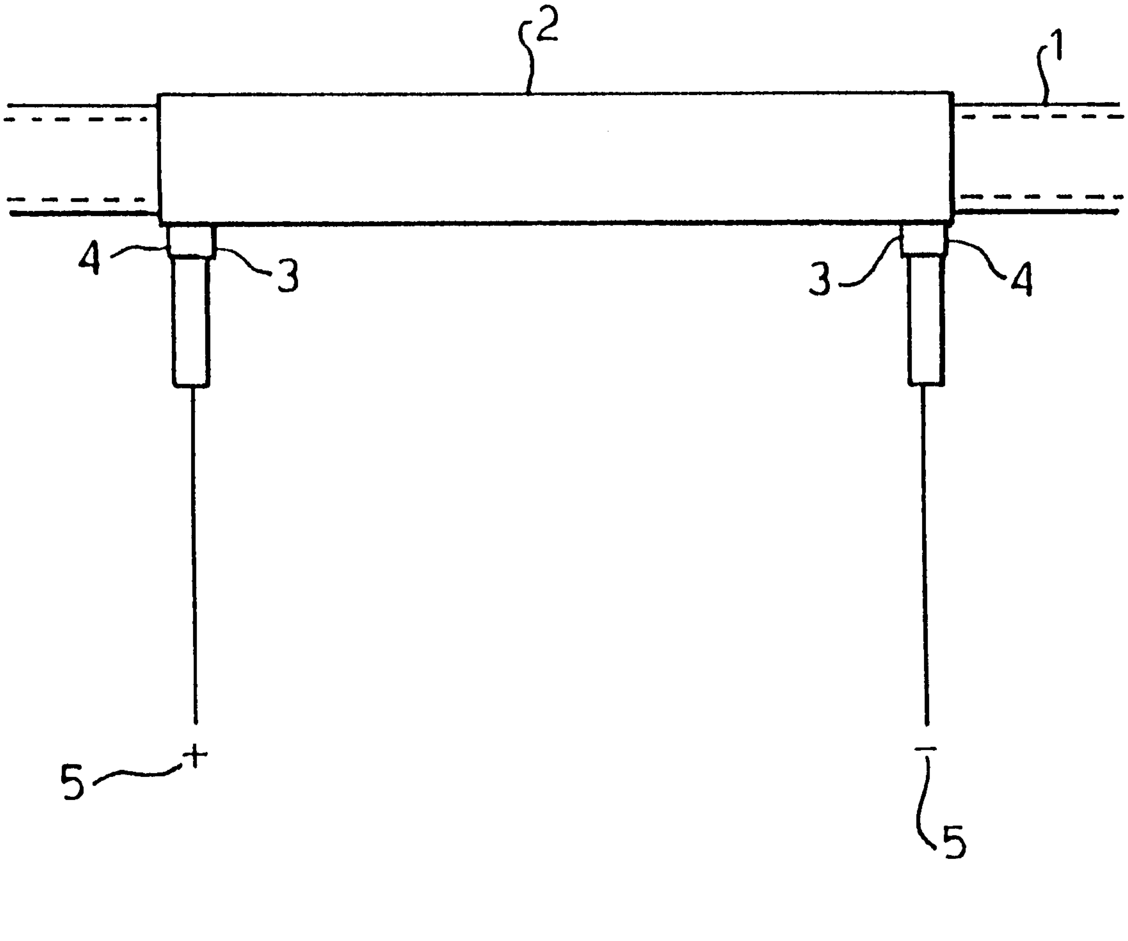
FIG. 4 Shows an apparatus for carrying out reactions involving multiple temperature stages and which utilises a strip of electrically conducting polymer to heat a capillary tube reaction vessel.

Referring to FIG. 4, a strip of electrically conducting polymer film 2 is wrapped around a capillary tube 1 and secured. The strip of polymer film 2 is provided with electrical connection points 3 to which an electrical supply 5 is connected via connection clips 4.

In use, current is passed through the polymer film 2, thereby heating the capillary tube 1 and any reagents placed inside the capillary tube 1.

Figure 5:
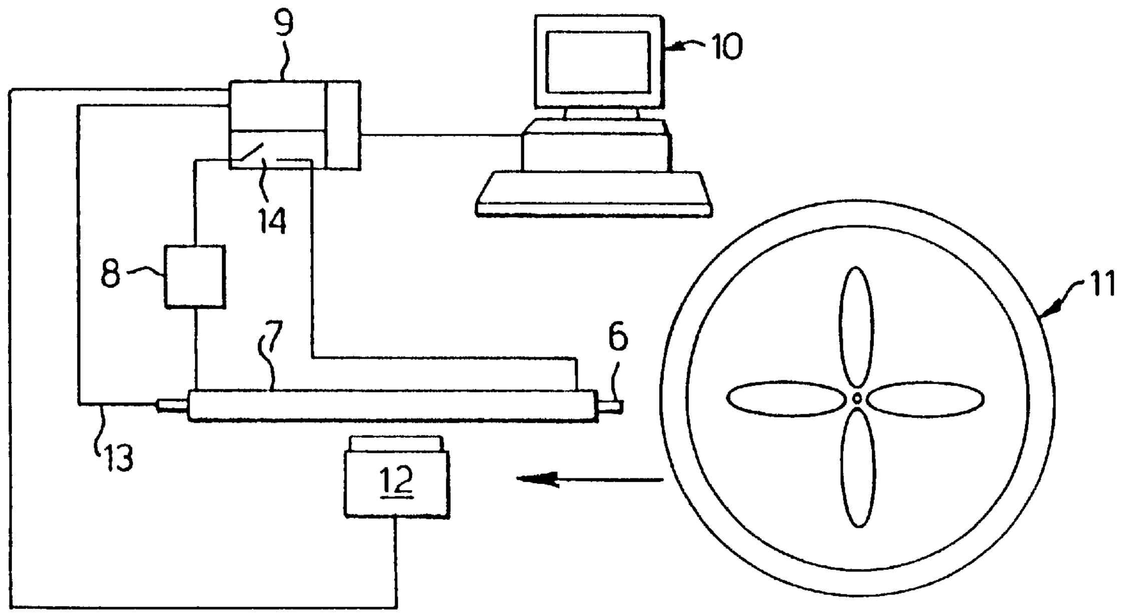
FIG. 5 shows a diagram of apparatus according to the invention for carrying out a PCR reaction.

The device of FIG. 5 was constructed in order to conduct PCR detections. A capillary tube 6 with a 1.12 mm internal diameter and 1.47 mm outer diameter was used as the reaction vessel. A strip of electrically conducting polymer 7 was wrapped around the tube and fastened so that it was held quite tightly to the external surface of the tube. Heating is therefore from all sides of the tubes 6 minimising the temperature gradient across a sample in the tube 6.

Heating was provided by an electrical power supply 8 which was connected via an interface 9 to a computer 10 to allow the heating cycles to be controlled automatically. A fan cooler 11 was arranged to direct air onto the polymer 7. An infra-red thermocouple 12 was provided on the outside of the polymer 7 in order to monitor the temperature.

For the purposes of assessing the performance of the apparatus prior to use, a K-type thermocouple was used to monitor the temperature inside the tube 6. The internal and external temperatures were then used to linearise the external temperature readings to the predicted sample temperature.

The heating polymer is connected to the power supply 8 and the circuit closed using the interface 9 and software. A switch 14 arranged to close the circuit was a fast optical relay which can switch every 10 ms. A second circuit was used to control two small electric fans 11 which provided forced air cooling of the reaction sample and which are run continuously. The control software was LabView which provides a user friendly graphical interface for both programming and operation. Current was applied initially with relatively high frequency in order the more rapidly to arrive at the required temperature. When the designated operating temperature was achieved the current was applied less frequently as required to maintain the designated operating temperature for the predetermined duration.

The apparatus shown in FIG. 7 comprises a lidded box 70 having insulative partitioning defining a plurality of detector element receptor bays 71. The box 71 is shown electrically connected via an interface unit 72 to a power source 73 and a computer 74. The connection is such as to permit different supplies to each of the bays 71. Each bay contains a thermocouple (not shown) for monitoring the temperature therein.

The detector element shown in FIG. 7*a* comprises a reaction tube 75 surrounded by a sheath 76. The sheath 76 is formed of a heating polymer and is connected to supply terminals 77 and 78.

After a tube 75 has been filled and stopped it can be offered to the appropriate bay 71 until the terminals 77 and 78 have clipped onto matching receptor terminals in the bays (not shown). The apparatus when fully connected is arranged to permit displaying on the computer screen the connection status of each tube 75.

Closure of the lid to the box 70 completes the insulation of each bay and the retention of each tube 75 in its bay.

The computer programme is arranged for the separate identification of the molecule being searched for in each tube 75, which done it is arranged for the control of the appropriate temperature cycle for PCR to amplify that molecule if present. When the cycles are complete the tube contents can be exposed to appropriate gene probe detectors to determine whether the molecule searched for was indeed present.

Alternatively it would be possible to utilise the apparatus to effect "real time quantitation" where the reaction is monitored throughout and not just at the end point.

Of course the principle of the apparatus described in relation to FIGS. 7 and 7*a* may be realised in a variety of ways. It can be mobile rather than portable and arranged for the reception of detector elements in a form other than that of a tube, including a slide. Typically, it is arranged to deal with 96 or 192 detector elements.

A preferred form of the reaction vessels of the invention are illustrated in FIGS. 8 to 12. The embodiment of FIG. 8 comprises a conical container (13) and a cap member (14) which projects into the container (13) so as to define a thin space (15) therebetween. A sealing strip (16) ensures that the cap member (14) effectively closes the container (13). A base portion (17) of the container (13) is flattened and made of an optically clear material so that contents of the space (15) may be observed. A sheath of electrically conducting polymer (18) is provided around the container (13). This is provided with electrical connections which may be connected to a power supply.

In use, reagents are introduced into the container (13) before application of the cap member (14). When the cap member (14) is applied, the reagents become distributed through the space (15). Current is then applied to the electrically conducting polymer sheath in order to heat the reaction vessel at it contents to the desired temperature.

The alternative embodiment of FIG. 9 shows a container (19) of generally circular cross section but with a flattened base. In this case, the lid (20) is provided with an upper portion (21), which snap fits onto the container (19). Once again a consistent thin space (22) is formed between the container (19) and the lid (20). If desired the upper portion (21) may comprise a lens which allows enhanced observation of contents of the container. Additionally or alternatively, the projecting portion the lid (20) may comprise an optical waveguide such as a fibre optic, which forms an integral part of the reaction monitoring system.

One of the container (19) or lid (21) may comprise an electrically conducting polymer which is connectable to a power supply (not shown). Alternatively, the container may be provided with a sheath of electrically conducting polymer (not shown).

This embodiment may be employed in a similar manner to the embodiment of FIG. 8 above.

The modification shown in FIG. 10 includes a differently shaped container (22) with a corresponding differently shaped lid (23) which snap fits onto the container (22). In this case however, the lid (23) includes a channel (24) which can accommodate a temperature monitoring device (25) such as a thermocouple or resistive temperature device (RTD), in order to allow the temperature of the reaction being effected in the container (22) to be monitored.

Again, the container (22) and/or the lid (23) may comprise an electrically conducting polymer, or a sheath of electrically conducting polymer may be provided around the container (22).

Although the lid (23) is solid, it may be hollowed out in an alternative embodiment (FIG. 11), in order to reduce the thermal mass. In this case, a sealing ring (16) is provided in order to enclose the space between the container (22) and the lid (23).

The embodiment of FIG. 12 illustrates a modification whereby the reaction effected in the vessel may be monitored readily. In this instance the container (26) is generally cylindrical in shape but has an annular projection (27) extending from the base surface thereof. A lid (28) is adapted to sit directly on the base of the container (26) such that the space defined therebetween is generally cylindrical (29). The container (26) may then be surrounded by a sheath of electrically conducting polymer for heating, and the vessel may optionally be placed in a cooling apparatus (not shown).

If the container is illuminated in the direction of the broad arrows, for example using a fluorescent excitation source, any sample in the container will be illuminated. Signal generated by the source may be monitored by an appropriate fluorescence monitoring device which is arranged in line with the projection (27) in the direction of the line arrows.

Various signals can be monitored simultaneously from different points around the annular projection (27). Alternatively, one or more capillary-like projections may be provided in place of the annular projection (27) so that different signals can be monitored from each. For instance, fluorescence at different wavelengths can be monitored. This may be the wavelengths of for example a reporter and a quencher molecule when these are used together in a reaction such as a TAQMAN™ reaction.

The following Example illustrates the invention.

EXAMPLE

Amplification of DNA

Using the apparatus of FIG. 5 with the K-type thermocouple removed, the following PCR reaction was effected.

A 100 base pair amplicon from a cloned *Yersinia pestis* fragment was amplified. Reaction conditions had previously been optimised using the Idaho RapidCycler™ and samples of the same reaction mixture were amplified in the Idaho RapidCycler™ as control reactions.

The reaction mixture placed in the tube 6 comprised the following:

50 mM Tris.HCl pH 8.3

3 mM $MgCl_2$ 2.5 mg/ml Bovine Serum Albumen

200 $\mu$M each of dATP, dTTP, dCTP and dGTP

10 $\mu$g/ml each PCR primers

25 Units/ml Taq Polymerase

Figure 6:
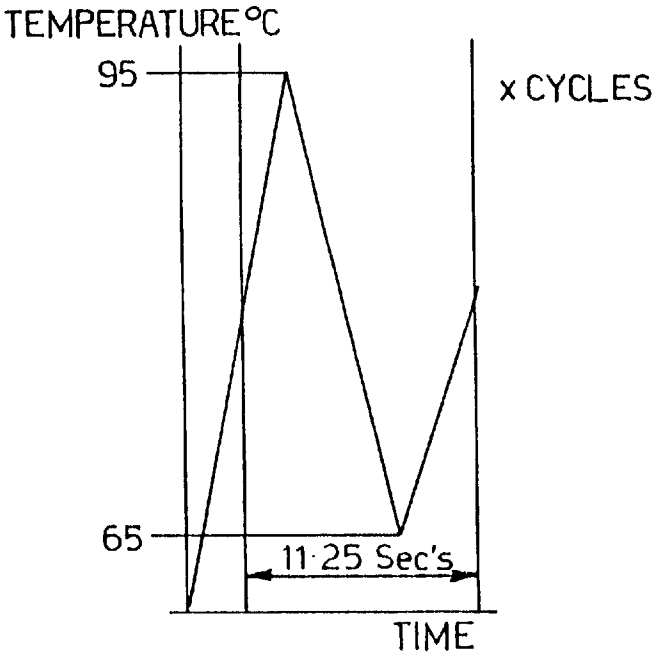
FIG. 6 shows a thermocycling profile used with the apparatus of FIG. 5.

The thermocycling profile was programmed as 95° C. for zero seconds, 55° C. for zero seconds, 72° C. for zero seconds as illustrated in FIG. 6. By way of comparison, a similar thermocycling profile was programmed into an Idaho RapidCycler™. Reaction volumes of 50 μl were used in both the polymer covered capillary vessel 6 and the Idaho RapidCycler™.

In this context, "zero seconds" means that as soon as the target temperature is reached, the program instructs the subsequent temperature to be induced. The precise time at which the reaction is held at the target temperature is therefore dependent upon the parameters and properties of the device used. In general however, it will be less than one second.

After 40 cycles in the capillary vessel, a 50 μl sample of the PCR product from each of the reactions were size fractionated by agarose gel electrophoresis in a 2% gel in 1×TAE buffer. DNA was visualised using ethidium bromide staining. The sample was run adjacent a sample from the Idaho RapidCycler™ (25 cycles) and a similar correctly sized amplicon was detected.

What is claimed is:

1. Apparatus for effecting reactions, said apparatus comprising a plurality of reaction vessels for holding reagents, an electrically conducting polymer which emits heat when an electric current is passed through it, and control means for controlling supply of current to the polymer, the polymer being connectable to an electrical supply via the control means, wherein different currents can be supplied to heat each vessel of said plurality or a group of vessels of said plurality, independently from one another.

2. Apparatus according to claim 1 wherein the control means is arranged for the supply of current for a different temperature and/or time profile for each of the reaction vessels.

3. Apparatus as claimed in claim 1 wherein each reaction vessel comprises a container for reactants and the heater polymer is contiguous with said container.

4. Apparatus as claimed in claim 3 wherein the heater polymer forms a sheath around the container.

5. Apparatus as claimed in claim 3 wherein the heater polymer is in the form of a film.

6. Apparatus as claimed in claim 4 wherein the sheath is integral with the container.

7. Apparatus as claimed in claim 3 wherein the heater polymer is perforated or reticulated.

8. Apparatus as claimed in claim 1 wherein the heater polymer forms a container for the reactants.

9. Apparatus as claimed in claim 1 wherein the reaction vessel comprises a container for reactants, wherein one of the surfaces of the container is coated with the said heater polymer.

10. Apparatus as claimed in claim 1 wherein each reaction vessel comprises a capillary tube.

11. Apparatus as claimed in claim 1 wherein the reaction vessel comprises a slide.

12. Apparatus as claimed in claim 1 wherein the reaction vessel comprises a chip.

13. Apparatus as claimed in claim 1 wherein the reaction vessels are provided in an array.

14. Apparatus as claimed in claim 1 wherein the reaction vessel comprises a container and a cap member, the cap member being formed so as to project into the container to reduce the capacity thereof and to create a space therebetween of substantially consistent proportions.

15. Apparatus as claimed in claim 1 wherein the control means is arranged to supply electric current so as to conduct reactions requiring multiple temperature stages within the reaction vessels.

16. Apparatus as claimed in claim 1 and wherein the control means is programmed such that multiple cycles of the reaction can be effected automatically.

17. Apparatus as claimed in claim 1 wherein the control means is arranged to supply current according to a predetermined time/temperature profile.

18. Apparatus as claimed in claims 1 and adapted for polymerase chain reaction processes.

19. Apparatus as claimed in claim 1 further comprising a means for detecting a signal from a sample in a reaction vessel.

20. A method of carrying out a chemical or biochemical reaction which requires multiple temperature stages; said method comprising placing reagents required for said reaction in a reaction vessel which comprises an electrically conducting polymer which emits heat when an electric current is passed through it, supplying current to said polymer so as to heat reagents to a first desired temperature; and thereafter adjusting the current so as to produce the subsequent temperatures stages required for the reaction.

21. A method according to claim 20 wherein the reaction is a DNA amplification method.

22. A method according to claim 21 wherein the amplification method is a polymerase chain reaction (PCR).

23. A method according to claim 19 wherein reagents for a plurality of reactions are each placed in a reaction vessel and heated simultaneously.

24. A method according to claim 23 wherein each reaction vessel is heated individually to the temperature required for the reaction taking place within that vessel.

25. A reaction vessel comprising a slide or a chip and an electrically conducting polymer which emits heat when an electric current is passed through it, said polymer being arranged to heat reactants on said slide or chip.

26. A reaction vessel according to claim 25 wherein the said polymer is integral with the slide or chip.

27. A reaction vessel comprising a container, a cap member, and an electrically conducting polymer which is arranged so as to heat reagents in the reaction vessel when current is supplied to said polymer, the cap member being formed so as to project into the container to reduce the capacity thereof and to create a space therebetween of substantially consistent proportions.

28. A reaction vessel according to claim 27 wherein the cap member is adapted to seal the container.

29. A reaction vessel according to claim 28 wherein the cap member is adapted to snap fit onto the container.

30. A reaction vessel according to claim 27 wherein the space created between the cap member and the container when the cap member is in place is of substantially similar proportions to a capillary tube.

31. A reaction vessel according to claim 27 wherein the space defined between the container and the lid member is from 0.4 to 1.2 mm at any point.

32. A reaction vessel according to claim 27 wherein the container is of right cylindrical form and the cap member is arranged to impinge upon the base so that the space created when the cap member is in place has the form of an open cylinder.

33. Apparatus for carrying out reactions at controlled temperatures, which apparatus comprises a reaction vessel as claimed in claim 28 and a means for controlling the supply of current to the electrically conducting polymer so as to controller temperature thereof.

34. Apparatus according to claim 33 which further comprises means for observing a signal generated in the space between the container and the cap member of the reaction vessel.

35. Apparatus for carrying out a reaction at controlled temperatures, which apparatus comprises a reaction vessel as claimed in claim 26 and a means for controlling the supply of electric current to the electricity conducting polymer so as to control the temperature thereof.

36. Apparatus according to claim 1 wherein the current is supplied to the polymer by induction.

37. Apparatus according to claim 36 which further comprises means for inducing the electric current comprises means for generating a magnetic or electrical field in the polymer.

38. A method according to claim 20 wherein current is induced in said polymer by exposure to an electrical or magnetic field.

* * * * *

UNITED STATES PATENT AND TRADEMARK OFFICE

CERTIFICATE OF CORRECTION

PATENT NO. : 6,312,886 B1
DATED : November 6, 2001
INVENTOR(S) : Lee et al.

It is certified that error appears in the above-identified patent and that said Letters Patent is hereby corrected as shown below:

Title page,
Item [75], should read:
-- [75] Inventors: Martin A. Lee, Hilary Bird and Dario Lyall Leslie, all of Salisbury (GB) --

Signed and Sealed this

Seventeenth Day of December, 2002

JAMES E. ROGAN
*Director of the United States Patent and Trademark Office*